US011331297B2

(12) United States Patent
Song et al.

(10) Patent No.: US 11,331,297 B2
(45) Date of Patent: May 17, 2022

(54) POLYOXOMETALATE COMPLEXES AND USES IN MANAGING CANCER

(71) Applicant: Emory University, Atlanta, GA (US)

(72) Inventors: Jie Song, Atlanta, GA (US); Shuming Nie, Atlanta, GA (US); Craig Hill, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/345,578

(22) PCT Filed: Oct. 26, 2017

(86) PCT No.: PCT/US2017/058563
§ 371 (c)(1),
(2) Date: Apr. 26, 2019

(87) PCT Pub. No.: WO2018/081442
PCT Pub. Date: May 3, 2018

(65) Prior Publication Data
US 2019/0262302 A1   Aug. 29, 2019

Related U.S. Application Data

(60) Provisional application No. 62/469,340, filed on Mar. 9, 2017, provisional application No. 62/413,404, filed on Oct. 26, 2016.

(51) Int. Cl.
*A61K 31/28* (2006.01)
*A61P 35/00* (2006.01)
(Continued)

(52) U.S. Cl.
CPC ............ *A61K 31/28* (2013.01); *A61K 31/282* (2013.01); *A61K 33/243* (2019.01); *A61P 35/00* (2018.01);
(Continued)

(58) Field of Classification Search
CPC .... A61K 31/28; A61K 31/282; A61K 33/243; A61K 47/02; A61K 9/143; A61P 35/00
See application file for complete search history.

(56) References Cited

U.S. PATENT DOCUMENTS

| 6,232,340 B1 | 5/2001 | Zhang |
| 6,911,470 B1 | 6/2005 | Schinazi |
| 2010/0305387 A1 | 12/2010 | Okun |

OTHER PUBLICATIONS

Bayaguud et al. Facile synthesis of an organically-derivatized hexavanadate containing the remote amino group, TBA2[V6O13{(OCH2)3CNH2}2] CrystEngComm, 2016, 18, 4042.
(Continued)

*Primary Examiner* — Savitha M Rao
(74) *Attorney, Agent, or Firm* — Emory Patent Group

(57) ABSTRACT

The disclosure relates polyoxometalate complexes and uses in the management, treatment, or prevention of cancer. In certain embodiments, the polyoxometalate complexes comprise polydentate oxygen bridging ligands such as those of the following formula: [POM{(OCH2)3CX}2], [M6O13{(OCH2)3CX}2], [V6O13 {(OCH2)3CX}2], salts, or derivatives thereof wherein POM is a polyoxometalate, M is a metal, and X is defined herein. In certain embodiments, the disclosure relates to pharmaceutical compositions comprising polyoxometalate complexes disclosed herein.

5 Claims, 6 Drawing Sheets

(51) Int. Cl.
| | |
|---|---|
| A61K 33/243 | (2019.01) |
| A61K 31/282 | (2006.01) |
| C07C 229/00 | (2006.01) |
| B32B 21/02 | (2006.01) |
| C09D 7/65 | (2018.01) |
| C09D 5/08 | (2006.01) |
| C09D 5/02 | (2006.01) |

(52) U.S. Cl.
CPC .......... *B32B 21/02* (2013.01); *C07C 229/00* (2013.01); *C09D 5/02* (2013.01); *C09D 5/08* (2013.01); *C09D 7/65* (2018.01)

(56) References Cited

OTHER PUBLICATIONS

Chen et al. Coordination Compounds of Polyoxovanadates with a Hexametalate Core. J. Am. Chem. Soc 1992, 114, 12, 4667-4681.

Laronze et al. A New Method to Prepare Transition Metal Salts of Bulk and Supported Heteropolyacids. Application to the Catalysis of the Oxidative Dehydrogenation of Isobutyric Acid, Journal of Cluster Science, 2002,13 (3):355-368.

Lee, Incorporation of Polyoxometalate With Gelatin and Their Feasibiity as an Anti-Cancer Drug, Georgia Institute of Technology 2013.

Li et al. Inorganic-Organic Hybrid Vesicles with Counterion- and pH-Controlled Fluorescent Properties, J. Am. Chem. Soc. 2011, 133, 14010-14016.

Massachusetts General Hospital, Why Cisplatin Kills Breast Cancer Cells When Other Drugs Fail, ScienceDaily, 2007, available at https://www.sciencedaily.com/releases/2007/04/070419172122.htm.

Shah et al. Cytotoxicity and enzyme inhibition studies of polyoxometalates and their chitosan nanoassemblies, Toxicology Reports 1 (2014) 341-352.

Yang et al. Polyoxometalate—biomolecule conjugates: A new approach to create hybrid drugs for cancer therapeutics, Bioorganic & Medicinal Chemistry Letters 23 (2013) 1462-1466.

European Patent Application No. 17864572.1 Communication dated Nov. 15, 2021 and Extended European Search Report.

Gao et al., Organic-functionalized, substituted polyoxovanadium and vanadoniobates: synthesis, structure, and application, Polyhedron, 2014, 83: 242-258.

Karimian et al. Dual functional hybrid-polyoxometalate as a new approach for multidrug delivery, Microporous and Mesoporous Materials, 2017, 274:23-30.

Zheng et al. Synthesis and Anti-HIV Activity of Bis(Methano Fullerene)Polyoxometalates, Electrochemical Society Proceedings, 1998, 8:1222-1226.

POLYOXOMETALATE COMPLEXES AND USES IN MANAGING CANCER

CROSS-REFERENCE TO RELATED APPLICATIONS

This application is the National Stage of International Application No. PCT/US2017/058563 filed Oct. 26, 2017, which claims the benefit of U.S. Provisional Application No. 62/413,404 filed Oct. 26, 2016 and U.S. Provisional Application No. 62/469,340 filed Mar. 9, 2017. The entirety of each of these applications is hereby incorporated by reference for all purposes.

STATEMENT REGARDING FEDERALLY SPONSORED RESEARCH OR DEVELOPMENT

This invention was made with government support under CA163256 awarded by the National Institutes of Health. The government has certain rights in the invention.

BACKGROUND

Many cancers become resistant to known chemotherapy agents. One of the most demanding public health challenges is to develop therapeutic strategies that address drug resistance. Modulation of oxidative stress has been reported as a therapeutic strategy against cancer. See Gorrini et al., Nat. Rev. Drug Discov. 12, 931-947 (2013). Reactive oxygen species (ROS) such superoxide, hydrogen peroxide, and the hydroxyl free radical are produced in cells, and elevated levels of ROS are present in cancer cells. Schumacker report ROS can initiate cancer, and strategic targeting of antioxidant systems may undermine survival of new tumor cells. Cancer Cell. 2015, 27(2):156-7.

Shah et al. report polyoxometalates (POMs) are potential anticancer agents. Toxicology Reports 1 (2014) 341-352. See also Wang et al. J Inorg Biochem, 94 (2003), pp. 279-284 and Mitsui et al. Biomed Pharmacother, 60 (2006), pp. 353-358.

Chen et al. report coordination compounds of polyoxovanadates with a hexametalate core. J. Am. Chem. Soc. 114, 4667-4681 (1992). Li et al. report inorganic—organic hybrid clusters synthesized from polyoxometalates. J. Am. Chem. Soc., 2011, 133 (35), pp 14010-14016.

References cited herein are not an admission of prior art.

SUMMARY

The disclosure relates polyoxometalate complexes and uses in the management, treatment, or prevention of cancer. In certain embodiments, the polyoxometalate complexes comprise polydentate oxygen bridging ligands such as those of the following formula: [POM{(OCH$_2$)$_3$CX}2], [M$_6$O$_{13}${(OCH$_2$)$_3$CX}$_2$], [V$_6$O$_{13}${(OCH$_2$)$_3$CX}$_2$], salts, or derivatives thereof wherein POM is a polyoxometalate, M is a metal, and X is defined herein. In certain embodiments, the disclosure relates to pharmaceutical compositions comprising polyoxometalate complexes disclosed herein.

In certain embodiments, this disclosure relates to methods of treating or preventing cancer comprising administering an effective amount of a polyoxometalate complex disclosed herein to a subject in need thereof. In certain embodiments, the subject is exhibiting symptoms of, or diagnose with cancer. In certain embodiments, the cancer is leukemia, lymphoma, melanoma, glioblastoma, cervical, ovarian, colon, breast, gastric, lung, skin, ovarian, pancreatic, prostate, head, neck, bladder, and renal cancer.

In certain embodiments, the polyoxometalate complex is administered in combination with a second chemotherapeutic agent. In certain embodiments, the second chemotherapy agent is a platinum-based antineoplastic, cisplatin, carboplatin, oxaliplatin, nedaplatin, triplatin tetranitrate, phenanthriplatin, picoplatin, satraplatin, or combinations thereof.

DETAILED DISCUSSION

Figure 1A:
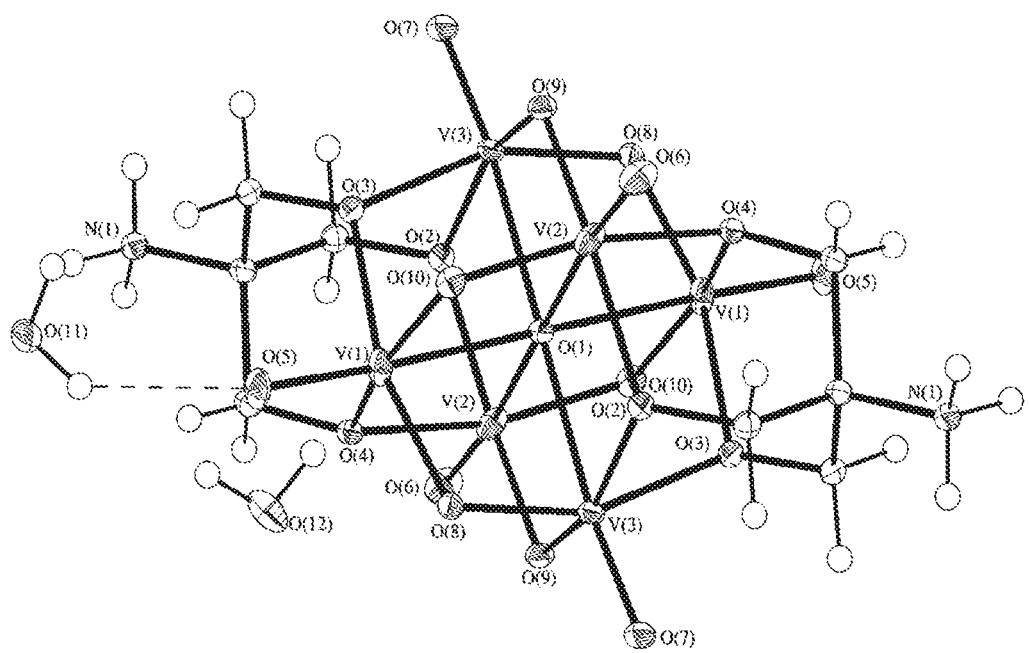
FIG. 1A shows an X-ray single crystal structure of [V$_6$O$_{13}${(OCH$_2$)$_3$CNH$_3$}$_2$](VPOA-6).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps. "Consisting essentially of" or "consists essentially" or the like, when applied to methods and compositions encompassed by the present disclosure refers to compositions like those disclosed herein that exclude certain prior art elements to provide an inventive feature of a claim, but which may contain additional composition components or method steps composition components or method steps, etc., that do not materially affect the basic and novel characteristic(s) of the compositions or methods, compared to those of the corresponding compositions or methods disclosed herein.

As used herein, "subject" refers to any animal, preferably a human patient, livestock, or domestic pet.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

A "linking group" refers to any variety of molecular arrangements that can be used to bridge to molecular moieties together. An example formula may be —$R_m$— wherein R is selected individually and independently at each occurrence as: —$CR_mR_m$—, —$CHR_m$—, —CH—, —C—, —$CH_2$—, —$C(OH)R_m$, —C(OH)(OH)—, —C(OH)H, —$C(Hal)R_m$—, —C(Hal)(Hal)-, —C(Hal)H—, —$C(N_3)$ $R_m$—, —$C(CN)R_m$—, —C(CN)(CN)—, —C(CN)H—, —$C(N_3)(N_3)$—, —$C(N_3)$H—, —O—, —S—, —N—, —NH—, —$NR_m$—, —(C=O)—, —(C=NH)—, —(C=S)—, —(C=$CH_2$)—, which may contain single, double, or triple bonds individually and independently between the R groups. If an R is branched with an $R_m$ it may be terminated with a group such as —$CH_3$, —H, —CH=$CH_2$, —CCH, —OH, —SH, —$NH_2$, —$N_3$, —CN, or -Hal, or two branched Rs may form a cyclic structure. It is contemplated that in certain instances, the total Rs or "m" may be less than 100 or 50 or 25 or 10. Examples of linking groups include bridging alkyl groups and alkoxyalkyl groups.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, hereby incorporated by reference.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Typical prodrugs are pharmaceutically acceptable esters. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate, and benzoate derivatives of an alcohol or acetamide, formamide, methanesulfonate, and benzamide derivatives of an amine functional group in the active compound and the like.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO$_2$Rb, —C(=O)Ra, —C(=O)ORa, —C(=O)NRaRb, —OC(=O)NRaRb, —ORa, —SRa, —SORa, —S(=O)$_2$Ra, —OS(=O)$_2$Ra and —S(=O)$_2$ORa. Ra and Rb in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

As used herein, "salts" refers the disclosed polyoxometalates comprising a counter ion, typically a cation such as quaternary amines. Examples of salts include, but are not limited to, mineral or organic acid salts of basic residues such as amines, alkylamines, dialkylamines or; alkali or organic salts of acidic residues such as carboxylic acids; and the like.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bridge (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above attached through a sulfamoyl bridge (i.e., —S(=O)$_2$NHalkyl), and an "Arylsulfamoyl" refers to an alkyl attached through a sulfamoyl bridge (i.e., —S=O)$_2$NHaryl).

"Alkylsulfinyl" refers to an alkyl as defined above with the indicated number of carbon atoms attached through a sulfinyl bridge (i.e. —S(=O)alkyl).

The terms "halogen" and "halo" refer to fluorine, chlorine, bromine, and iodine.

Polyoxometalate Complexes Having Polydentate Oxygen Bridging Ligands

In certain embodiments, this disclosure relates to polyoxometalate complexes comprising polydentate oxygen bridging ligands. In certain embodiments, the ligands are $(OL)_3CX$ or $(OCH_2)_3CX$ wherein X is $CR^1R^2R^3$, $NR^1R^2$, $N^+R^1R^2R^3$, $NO_2$, or combinations thereof; L is $CH_2$ or other linking group, and $R'R^2R^3$ are described herein. In certain embodiments, the polyoxometalate complexes have structures of the following formula:

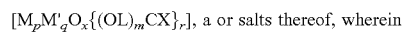

$[M_pM'_qO_x\{(OL)_mCX\}_r]$, a or salts thereof, wherein

X is $CR_1R^2R^3$, $NR^1R^2$, $N^+R^1R^2R^3$, $NO_2$, or combinations thereof;

L is $CH_2$ or other linking group;

M is a metal atom typically a d0 center, such as tungsten (W), molybdenum (Mo), vanadium (V), niobium (Nb), tantalum (Ta), or combinations thereof;

M' is one or more redox active metals atoms selected from f-block elements, d-block elements, or combinations thereof;

p is an integer from 0 to 50;

q is an integer from 0 to 40; wherein the sum of p and q is two or more;

x is an integer from 0 to 400;

n is 1, 2, or 3;

m is an integer 2 or 3;

r is an integer from 2 to 25;

$R^1$, $R^2$, and $R^3$ are each the same or different at occurrence hydrogen, alkyl, amino, formyl, carboxy, alkanoyl, carbamoyl, alkylsulfinyl, alkylsulfonyl, arylsulfonyl, carbocyclyl, aryl, or heterocyclyl, wherein each $R^1$, $R^2$, and $R^3$ are optionally substituted with one or more, the same or different, $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methyl sulfamoyl, N-ethyl sulfamoyl, N,N-dimethylsulfamoyl, N,N-diethylsulfamoyl, N-methyl-N-ethylsulfamoyl, carbocyclyl, aryl, or heterocyclyl.

In certain embodiments, wherein r is 2.

In certain embodiments, M is V.

In certain embodiments, the polyoxometalate complexes have comprises structures of the following formula:

$[M_pM'_qO_x\{(OCH_2)_3CX\}_r]$, salts, or derivatives thereof, wherein

X is $CR^1R^2R^3$, $NR^1R^2$, $N^+R^1R^2R^3$, $NO_2$, or combinations thereof;

M is a metal atom typically a d0 center, such as tungsten (W), molybdenum (Mo), vanadium (V), niobium (Nb), tantalum (Ta), or combinations thereof;

M' is one or more redox active metals atoms selected from f-block elements, d-block elements, or combinations thereof;

p is an integer from 0 to 50;

q is an integer from 0 to 40; wherein the sum of p and q is two or more;

x is an integer from 0 to 400;

n is 1, 2, or 3;

m is an integer 2 or 3;

r is an integer from 2 to 25;

$R^1$, $R^2$, and $R^3$ are each the same or different at occurrence hydrogen, halogen, alkyl, amino, formyl, carboxy, alkanoyl, carbamoyl, alkylsulfinyl, alkylsulfonyl, arylsulfonyl, carbocyclyl, aryl, or heterocyclyl, wherein each $R^1$, $R^2$, and $R^3$ are optionally substituted with one or more, the same or different, $R^{10}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the polyoxometalate complexes have comprises structures of the following formula:

$[M_pM'_qO_x\{(OCH_2)_3CX\}_2]$, salts, or derivatives thereof, wherein

X is $CR^1R^2R^3$, $NR^1R^2$, $N^+R^1R^2R^3$, $NO_2$, or combinations thereof;

M is a metal atom typically a d0 center, such as tungsten (W), molybdenum (Mo), vanadium (V), niobium (Nb), tantalum (Ta), or combinations thereof;

M' is one or more redox active metals atoms selected from f-block elements, d-block elements, or combinations thereof;

p is an integer from 0 to 50;

q is an integer from 0 to 40; wherein the sum of p and q is two or more;

x is an integer from 0 to 400;

n is 1, 2, or 3;

m is an integer 2 or 3;

r is an integer from 2 to 25;

$R^1$, $R^2$, and $R^3$ are each the same or different at occurrence hydrogen, alkyl, amino, formyl, carboxy, alkanoyl, carbamoyl, alkylsulfinyl, alkylsulfonyl, arylsulfonyl, carbocyclyl, aryl, or heterocyclyl, wherein each $R^1$, $R^2$, and $R^3$ are optionally substituted with one or more, the same or different, $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the polyoxometalate complexes have comprises structures of the following formula:

$[POM\{(OCH_2)_3CX\}_2]$, salts, or derivatives thereof wherein

POM is a polyoxometalate;

X is $CR^1R^2R^3$, $NR^1R^2$, $N^+R^1R^2R^3$, or $NO_2$;

$R^1$, $R^2$, and $R^3$ are each the same or different at occurrence hydrogen, alkyl, hydroxy, amino, formyl, carboxy, alkanoyl, carbamoyl, alkylsulfinyl, alkyl sulfonyl, arylsulfonyl, carbocyclyl, aryl, or heterocyclyl, wherein each $R^1$, $R^2$, and $R^3$ are optionally substituted with one or more, the same or different, $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethyl sulfamoyl, N,N-diethylsulfamoyl, N-methyl-N-ethylsulfamoyl, carbocyclyl, aryl, or heterocyclyl.

In certain embodiments, the polyoxometalate complexes have comprises structures of the following formula:

[$V_6O_{13}${(OCH$_2$)$_3$CX}$_2$], salts, or derivatives thereof wherein

X is $CR^1R^2R^3$, $NR^1R^2$, $N^+R^1R^2R^3$, or $NO_2$;

$R^1$, $R^2$, and $R^3$ are each the same or different at occurrence hydrogen, alkyl, hydroxy, amino, formyl, carboxy, alkanoyl, carbamoyl, alkyl sulfinyl, alkyl sulfonyl, arylsulfonyl, carbocyclyl, aryl, or heterocyclyl, wherein each $R^2$, and $R^3$ are optionally substituted with one or more, the same or different, $R^{10}$;

$R^{10}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkyl sulfinyl, alkyl sulfonyl, arylsulfonyl, carbocyclyl, aryl, or heterocyclyl, wherein $R^{10}$ is optionally substituted with one or more, the same or different, $R^{11}$; and $R^{11}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethyl sulfinyl, mesyl, ethyl sulfonyl, methoxycarbonyl, ethoxycarbonyl, N-methylsulfamoyl, N-ethylsulfamoyl, N,N-dimethyl sulfamoyl, N,N-diethylsulfamoyl, N-methyl-N-ethylsulfamoyl, carbocyclyl, aryl, or heterocyclyl.

In certain embodiments, $M_pM'_q$ is (Co$_4$), (Ni$_4$), (Ni$_5$), (W$_{10}$), (Mo$_7$), (V$_6$), (V$_{10}$), (Ru$_3$), (Ru$_4$), (CoMo$_6$), (Co$_2$Mo$_{10}$) (SiW$_9$), (SiW$_{10}$), (Co$_4$SiW$_9$), (RuSiW$_{11}$), (GeW$_9$), (RuGeW$_{11}$), (PW$_9$), (AsW$_9$), (GeNb$_{12}$), or combinations thereof.

In certain embodiments M' is a transition metal selected from titanium, chromium, manganese, cobalt, iron, nickel, copper, rhodium, silver, iridium, palladium, platinum, mercury, ruthenium, and vanadium.

In certain embodiments, polyoxometalate complexes have the following formula: [$V_6O_{13}${(OCH$_2$)$_3$CNH$_3$}$_2$], [$V_6O_{13}${(OCH$_2$)$_3$CNO$_2$}$_2$], [$V_6O_{13}${(OCH$_2$)$_3$CCH$_2$OH}$_2$], [$V_6O_{13}${(OCH$_2$)$_3$CCH$_3$}$_2$], salts, or derivatives thereof.

Uses in Managing Cancer

In certain embodiments, this disclosure relates to methods of treating or preventing cancer comprising administering an effective amount of a polyoxometalate complex disclosed herein to a subject in need thereof. In certain embodiments, the subject is exhibiting symptoms of, or diagnose with cancer. In certain embodiments, the cancer is leukemia, lymphoma, melanoma, glioblastoma, cervical, ovarian, colon, breast, gastric, lung, skin, ovarian, pancreatic, prostate, head, neck, bladder, and renal cancer.

In certain embodiment, this disclosure relates to methods for the treatment a subject at risk of, exhibiting symptoms of, suspected of, or diagnosed with a cancer or neoplasm selected from skin cancer, melanoma, Barret's adenocarcinoma; billiary tract carcinomas; breast cancer; cervical cancer; cholangiocarcinoma; central nervous system tumors including primary CNS tumors such as glioblastomas, astrocytomas (including glioblastoma multiforme) and ependymomas, and secondary CNS tumors (i.e., metastases to the central nervous system of tumors originating outside of the central nervous system), colorectal cancer, including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; and thyroid cancers.

In certain embodiments, this disclosure relates to the use of a polyoxometalate complex disclosed herein for the preparation of a medicament for the treatment of Barret's adenocarcinoma; billiary tract carcinomas; breast cancer; cervical cancer; cholangiocarcinoma; central nervous system tumors including primary CNS tumors such as glioblastomas, astrocytomas (e.g., glioblastoma multiforme) and ependymomas, and secondary CNS tumors (i.e., metastases to the central nervous system of tumors originating outside of the central nervous system); colorectal cancer including large intestinal colon carcinoma; gastric cancer; carcinoma of the head and neck including squamous cell carcinoma of the head and neck; hematologic cancers including leukemias and lymphomas such as acute lymphoblastic leukemia, acute myelogenous leukemia (AML), myelodysplastic syndromes, chronic myelogenous leukemia, Hodgkin's lymphoma, non-Hodgkin's lymphoma, megakaryoblastic leukemia, multiple myeloma and erythroleukemia; hepatocellular carcinoma; lung cancer including small cell lung cancer and non-small cell lung cancer; ovarian cancer; endometrial cancer; pancreatic cancer; pituitary adenoma; prostate cancer; renal cancer; sarcoma; skin cancers including melanomas; and thyroid cancers, or any subset thereof, in a mammal (e.g., human).

The polyoxometalate complexes disclosed herein can be used alone in the treatment of each of the foregoing conditions or can be used to provide additive or potentially synergistic effects with certain existing chemotherapies, radiation, biological or immunotherapeutics (including monoclonal antibodies) and vaccines.

The precise therapeutically effective amount of the polyoxometalate complexes of this disclosure will depend on a number of factors. There are variables inherent to the polyoxometalate complexes including, but not limited to, the following: molecular weight, absorption, bioavailability, distribution in the body, tissue penetration, half-life, metabolism, protein binding, and excretion. These variables determine what dose of polyoxometalate complex needs to be administered in a sufficient percentage and for a sufficient amount of time to have the desired effect on the condition being treated (e.g., neoplasm). The duration of drug exposure will be limited only by the polyoxometalate complex half-life, and side effects from treatment requiring cessation of dosing. The amount of polyoxometalate complex administered will also depend on factors related to patients and disease including, but not limited to, the following: the age, weight, concomitant medications and medical condition of the subject being treated, the precise condition requiring treatment and its severity, the nature of the formulation, and the route of administration. Ultimately, the dose will be at the discretion of the attendant physician or veterinarian. Typically, the polyoxometalate complex disclosed herein will be given for treatment in the range of 0.01 to 30 mg/kg body weight of recipient (mammal) per day or per dose or per cycle of treatment and more usually in the range of 0.1 to 10 mg/kg body weight per day or per dose or per cycle of treatment. Thus, for an adult human being treated for a condition, the actual amount per day or per dose or per cycle of treatment would usually be from 1 to 2000 mg and this amount may be given in a single or multiple doses per day or per dose or per cycle of treatment. The full spectrum of dosing regimens may be employed ranging from continuous dosing (with daily doses) to intermittent dosing. It is envisaged that similar dosages would be appropriate for treatment of the susceptible neoplasms described above.

Combination Therapies

In certain embodiments, the polyoxometalate complex is administered in combination with a second chemotherapeutic agent. In certain embodiments, the second chemotherapy agent is a platinum-based antineoplastic, cisplatin, carboplatin, oxaliplatin, nedaplatin, triplatin tetranitrate, phenanthriplatin, picoplatin, satraplatin, or combinations thereof. In certain embodiments, the second chemotherapy agent is atezolizumab, avelumab, durvalumab, pembrolizumab, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol anastrozole, letrozole, vorazole, exemestane, finasteride, marimastat, trastuzumab, cetuximab, dasatinib, imatinib, ipilimumab, bevacizumab, combretastatin, thalidomide, and/or lenalidomide or combinations thereof.

In certain embodiments, methods disclosed herein may be combined with other anti-cancer, biologic, hormonal, antibody and supportive care agents. Supportive care agents include analgesics, anti-emetics and agents used to treat heamatologic side effects such as neutropenia. Analgesics are well known in the art. Anti-emetics include but are not limited to 5HT3 antagonists such as ondansetron, granisetron, dolasetron, palonosetron and the like; prochlorperazine; metaclopromide; diphenhydramine; promethazine; dexamethasone; lorazepam; haloperidol; dronabinol; olanzapine; and neurokinin-1 antagonists such as aprepitant, fosaprepitant and casopitant administered alone or in various combinations.

The polyoxometalate complexes disclosed herein and at least one additional anti-cancer or supportive care therapy may be employed in combination concomitantly or sequentially in any therapeutically appropriate combination. The administration of a polyoxometalate complex disclosed herein with one or more other anti-cancer agents may be in combination in accordance with the disclosure by administration concomitantly in one unitary pharmaceutical composition including both or all polyoxometalate complexes or two or more separate pharmaceutical compositions each including one or more of the compounds. The components of the combination may be administered separately in a sequential manner wherein one active ingredient is administered first and the other(s) second or vice versa. Such sequential administration may be close in time or remote in time.

When a polyoxometalate complex disclosed herein is used in combination with an anti-cancer and/or supportive care agent, the dose of each compound may differ from that when the compound is used alone. Appropriate doses will be readily appreciated by those skilled in the art. The appropriate dose of the polyoxometalate complex(es) disclosed herein and the other therapeutically active agent(s) and the relative timings of administration will be selected in order to achieve the desired combined therapeutic effect, and are within the expertise and discretion of the attendant clinician.

Typically, any chemotherapeutic agent that has activity against a susceptible neoplasm being treated may be utilized in combination with the polyoxometalate complexes disclosed herein, provided that the particular agent is clinically compatible with therapy employing a polyoxometalate complex disclosed herein. Typical anti-cancer agents useful in the present disclosure include, but are not limited to: alkylating agents, anti-metabolites, antitumor antibiotics, antimitotic agents, topoisomerase I and II inhibitors, hormones and hormonal analogues; retinoids, signal transduction pathway inhibitors including inhibitors of cell growth or growth factor function, angiogenesis inhibitors, and serine/threonine or other kinase inhibitors; cyclin dependent kinase inhibitors; antisense therapies and immunotherapeutic agents, including monoclonals, vaccines or other biological agents.

Alkylating agents are non-phase specific anti-cancer agents and strong electrophiles. Typically, alkylating agents form covalent linkages, by alkylation, to DNA through nucleophilic moieties of the DNA molecule such as phosphate, amino, and hydroxyl groups. Such alkylation disrupts nucleic acid function leading to cell death. Alkylating agents may be employed in combination with the polyoxometalate complexes disclosed herein in the compositions and methods described above. Examples of alkylating agents include but are not limited to nitrogen mustards such as cyclophosphamides, temozolamide, melphalan, and chlorambucil; oxazaphosphorines; alkyl sulfonates such as busulfan; nitrosoureas such as carmustine; triazenes such as dacarbazine; and platinum coordination complexes such as cisplatin, oxaliplatin and carboplatin.

Antimetabolite cancer agents are phase specific anticancer agents that act at S phase (DNA synthesis) of the cell cycle by inhibiting DNA synthesis or by inhibiting purine or pyrimidine base synthesis and thereby limiting DNA synthesis. The end result of discontinuing S phase is cell death. Antimetabolite cancer agents may be employed in combination with the polyoxometalate complexes disclosed herein in the compositions and methods described above. Examples of antimetabolite anti-cancer agents include but are not limited to purine and pyrimidine analogues and anti-folate compounds, and more specifically, hydroxyurea, cytosine, arabinoside, ralitrexed, tegafur, fluorouracil (e.g., 5FU), methotrexate, cytarabine, mercaptopurine and thioguanine.

Antitumor antibiotic agents are non-phase specific agents, which bind to or intercalate with DNA. Typically, such action disrupts ordinary function of the nucleic acids, leading to cell death. Antitumor antibiotics may be employed in combination with the polyoxometalate complexes disclosed herein in the compositions and methods described above. Examples of antitumor antibiotic agents include, but are not limited to, actinomycins such as dactinomycin; anthracyclines such as daunorubicin, doxorubicin, idarubicin, epirubicin and mitoxantrone; mitomycin C and bleomycins.

Antimicrotubule or antimitotic agents are phase specific agents active against the microtubules of tumor cells during M or the mitosis phase of the cell cycle. Antimitotic agents may be employed in combination with the polyoxometalate complexes disclosed herein in the compositions and methods described above. Examples of antimitotic agents include, but are not limited to, diterpenoids, *vinca* alkaloids, polo-like kinase (Plk) inhibitors and CenpE inhibitors. Examples of diterpenoids include, but are not limited to, paclitaxel and its analog docetaxel. Examples of *vinca* alkaloids include, but are not limited to, vinblastine, vincristine, vindesine and vinorelbine. Plk inhibitors are discussed further below.

Topoisomerase inhibitors include inhibitors of Topoisomerase II and inhibitors of Topoisomerase I. Topoisomerase II inhibitors, such as epipodophyllotoxins, are anti-cancer agents derived from the mandrake plant, that typically affect cells in the S and G2 phases of the cell cycle by forming a ternary complex with topoisomerase II and DNA, causing DNA strand breaks. The strand breaks accumulate and cell death follows. Examples of epipodophyllotoxins include, but are not limited to, etoposide and teniposide. Camptothecins, including camptothecin and camptothecin derivatives, are available or under development as Topoisomerase I inhibitors. Examples of camptothecins include, but are not limited to amsacrine, irinotecan, topotecan, and the various optical forms of 7-(4-methylpiperazino-methylene)-10,11-ethylenedioxy-20-camptothecin. Topoisomerase inhibitors may be employed in combination with the polyoxometalate complexes disclosed herein in the compositions and methods described above.

Hormones and hormonal analogues are useful compounds for treating cancers in which there is a relationship between the hormone(s) and growth and/or lack of growth of the cancer. Antitumor hormones and hormonal analogues may be employed in combination with the polyoxometalate complexes disclosed herein in the compositions and methods described above. Examples of hormones and hormonal analogues believed to be useful in the treatment of neoplasms include, but are not limited to antiestrogens, such as tamoxifen, toremifene, raloxifene, fulvestrant, iodoxyfene and droloxifene; anti-androgens; such as flutamide, nilutamide, bicalutamide and cyproterone acetate; adrenocorticosteroids such as prednisone and prednisolone; aminoglutethimide and other aromatase inhibitors such as anastrozole, letrazole, vorazole, and exemestane; progestrins such as megestrol acetate; 5alpha-reductase inhibitors such as finasteride and dutasteride; and gonadotropin-releasing hormones (GnRH) and analogues thereof, such as Leutinizing Hormone-releasing Hormone (LHRH) agonists and antagonists such as goserelin luprolide, leuprorelin and buserelin.

Examples of specific retinoids that may be used in combination with the polyoxometalate complexes disclosed herein include: retinoic acid; all-trans-retinoic acid ("ATRA" also known as "tretinoin"); tamibarotene ("Am80"); 9-cis-retinoic acid ((2E,4E,6Z,8E)-3,7-Dimethyl-9-(2,6,6-trimethylcyclohex-1-enyl)nona-2,4,6,-8-tetraenoic Acid) (also known as "9-cis-Tretinoin") (available from Sigma); Isotretinoin ((2Z,4E,6E,8E)-3,7-dimethyl-9-(2,6,6-trimethyl-1-cyclohexenyl)nona-2,4,6,-8-tetraenoic acid) (also known as "13-cis-retinoic acid") (ACCUTANE'); Am580 (4-(5,6,7,8-tetrahydro-5,5,8,8-tetramethyl-2-naphtamido) benzoic acid), See, M. Gianni, Blood 1996 87(4): 1520-1531; TTNPB (4-[E-2-(5,6,7,8-Tetrahydro-5,5,8,8-tetramethyl-2-naphthalenyl)-1-propeny-1]benzoic acid) (also known as "Ro 13-7410") See, M. F. Boehm et al. J. Med. Chem. 1994 37:2930 and R. P. Bissonnette et al., Mol. Cell. Biol. 1995 15:5576; and BMS753 (4-[[(2,3-dihydro-1,1,3, 3-tetramethyl-2-oxo-1H-inden-5-yl)carbonyl]amino]-benzoic acid) See, U.S. Pat. No. 6,184,256.

Several inhibitors of growth factor receptors are under development and include ligand antagonists, antibodies, tyrosine kinase inhibitors, anti-sense oligonucleotides and aptamers. Any of these growth factor receptor inhibitors may be employed in combination with the polyoxometalate complexes disclosed herein in any of the compositions and methods/uses described herein. Trastuzumab is an example of an anti-erbB2 antibody inhibitor of growth factor function. One example of an anti-erbB1 antibody inhibitor of growth factor function is cetuximab. Bevacizumab is an example of a monoclonal antibody directed against VEGFR. Examples of small molecule inhibitors of epidermal growth factor receptors include but are not limited to lapatinib and erlotinib. Imatinib is one example of a PDGFR inhibitor. Examples of VEGFR inhibitors include pazopanib, ZD6474, AZD2171, PTK787, sunitinib and sorafenib.

In certain embodiments, polyoxometalate complexes disclosed herein can be used and formulated in combination with the anti-cancer agents that are PD-1 antibodies such as nivolumab, pembrolizumab, pidilizumab, atezolizumab or CTLA-4 antibodies such as ipilimumab and tremelimumab.

Pharmaceutical Compositions

In certain embodiments, the disclosure relates to pharmaceutical compositions comprising particles disclosed herein and a pharmaceutically acceptable excipient or carrier. In certain embodiments, the disclosure contemplates pharmaceutical compositions comprising a polyoxometalate complex disclosed herein and a pharmaceutically acceptable excipient. In certain embodiments, the pharmaceutical compositions disclosed herein are in the form of a pill, capsule, tablet optionally comprising an enteric coating, micronized particle optionally comprising an enteric coating, or an aqueous buffer solution.

In certain embodiments, the pharmaceutically acceptable excipient is selected from a polyethylene glycol, propylene glycol saccharide, polysaccharide, sucrose, lactose, sorbic acid, starch, talc, cellulose, microcrystalline cellulose, a cellulose ether, hydroxypropyl cellulose, hydroxypropyl methyl cellulose, methyl cellulose, croscarmellose sodium, carboxymethylcellulose, xylitol, sorbitol, maltitol, mannitol.

In certain embodiments, the pharmaceutically acceptable excipient is selected from a calcium salt, calcium stearate, magnesium stearate, calcium phosphate, silicone dioxide, iron oxide, magnesium oxide, titanium dioxide, sodium lauryl sulfate, and stearic acid or salt thereof.

In certain embodiments, the pharmaceutically acceptable excipient is selected from gelatin, crosspovidone, povidone, and a paraben.

Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

In certain embodiments, the composition is an aqueous buffer or aqueous phosphate buffer solution, e.g., a pH between 6 and 8. Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Pharmaceutical compositions disclosed herein can be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids.

When the polyoxometalate complexes of the disclosure contain an acidic group as well as a basic group, the polyoxometalate complexes of the disclosure can also form internal salts, and such polyoxometalate complexes are within the scope of the disclosure. When a polyoxometalate complex contains a hydrogen-donating heteroatom (e.g. NH), salts are contemplated to cover isomers formed by transfer of the hydrogen atom to a basic group or atom within the molecule.

The polyoxometalate complexes described herein can be administered in the form of prodrugs. A prodrug can include a covalently bonded carrier that releases the active parent drug when administered to a mammalian subject. Prodrugs can be prepared by modifying functional groups present in the polyoxometalate complexes in such a way that the modifications are cleaved, either in routine manipulation or in vivo, to the parent polyoxometalate complexes. Prodrugs include, for example, polyoxometalate complexes wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the polyoxometalate complexes. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of a polyoxometalate complex and a suitable pharmaceutical acceptable carrier. The preparations can be prepared in a manner known per se, which usually involves mixing the at least one polyoxometalate complex according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

Generally, for pharmaceutical use, the polyoxometalate complexes can be formulated as a pharmaceutical preparation comprising at least one polyoxometalate complex and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one polyoxometalate complex of the disclosure e.g., about 10, 25, 50, 100, 200, 300 or 400 mg per unit dosage.

The polyoxometalate complexes can be administered by a variety of routes including the oral, ocular, rectal, transdermal, subcutaneous, intravenous, intramuscular or intranasal routes, depending mainly on the specific preparation used. The polyoxometalate complex will generally be administered in an "effective amount," by which it is meant any amount of a polyoxometalate complex that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which can be administered as a single daily dose, divided over one or more daily doses. The amount(s) to be administered, the route of administration and the further treatment regimen can be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Formulations containing one or more of the polyoxometalate complexes described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins, zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP.

Stabilizers are used to inhibit or retard drug decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine, and lauryl sulfobetaine.

If desired, the tablets, beads, granules, or particles can also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation.

Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

EXPERIMENTAL

Nanocluster with Potent Catalytic and Antitumor Activities

An zwitterionic nanocluster, $[V_6O_{13}\{(OCH_2)_3CNH_3\}_2]$ (VPOA-6) with a size of ca. 1 nm (FIG. 1A), is an example of potent inorganic drug targeting oxidative stress for selective killing of cancer cells. VPOA-6 significantly inhibits growth of the highly aggressive human cervical carcinoma KB-3-1 on xenografted mouse models while exhibiting no appreciable organ toxicity.

Figure 1B:
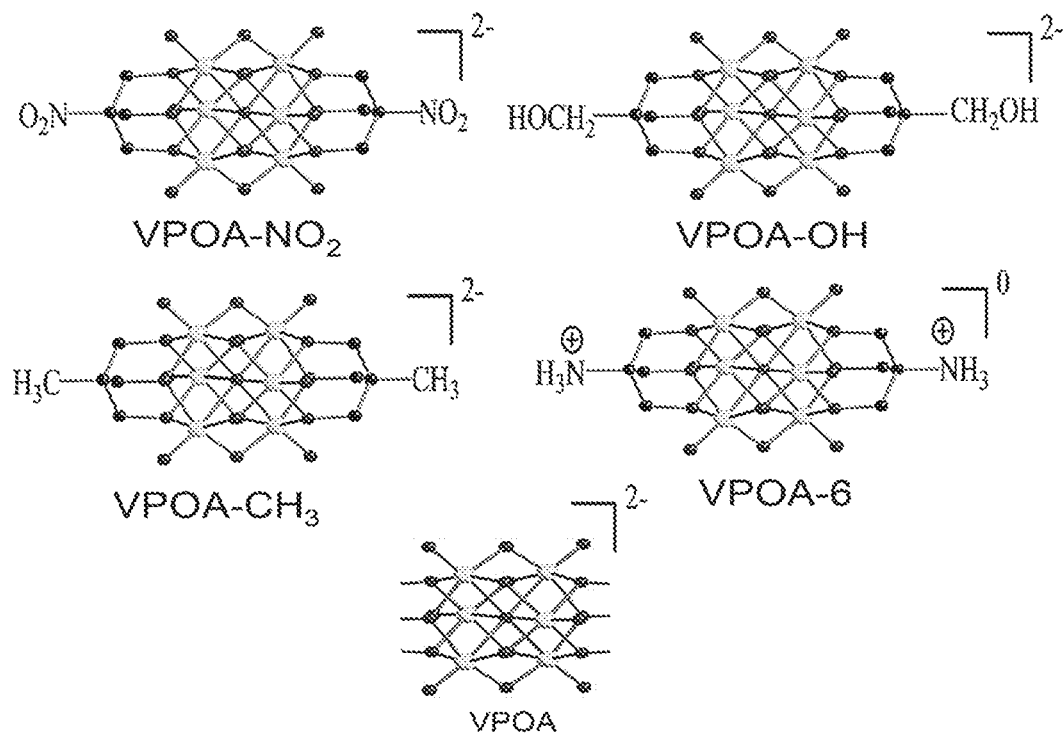
FIG. 1B illustrates structures of four hexavanadate analogues (VPOA-NO2, VPOA-OH, VPOA-CH3, and zwitterionic VPOA-6) in ball-and-stick representations—oxygen; vanadium; carbon. Some hydrogen atoms and TBA cations have been omitted for clarity.

Eight polyoxoanions were synthesized of various compositions and structures for the assessment of toxicity: $Na_3PMo_{12}O_{40}$, $K_5AlW_{12}O_{40}$, $Na_6P_2Mo_{18}O_{62}$, $Na_6P_2W_{18}O_{62}$, and four vanadium-containing analogues, VPOA-NO2, VPOA-OH, VPOA-Me and VPOA-6. The latter share the same $\{V_6O_{19}\}$ hexavanadate core and vary only in the terminal function group (FIG. 1A and FIG. 1B). The zwitterionic VPOA-6 stands out from cellular toxicity tests ($IC_{50}$=3.45 µM, KB-3-1 cell lines) and has been down-selected for further investigation. Structure of VPOA-6. The VPOA-6 zwitterion is derived from the spontaneous protonation of its precursor, the tetrabutylammonium (TBA) salt of hexavanadate, at physiological pH.

X-ray crystallographic determination (FIG. 1A) shows that this unit is a Linqvist type hexavanadate, in which six vanadium (V) centers are connected by nineteen oxygen atoms to form a nanoscale superoctahedral cluster core $\{V_6O_{19}\}$. This inorganic core is stabilized by two chelating tris(hydroxymethyl)aminomethane (tris-type) ligands that reside symmetrically on each side of this core, each bearing a protonated primary amine. Thus under physiological conditions and the conditions in this study, VPOA-6 exists as a zwitterion with both apical amines present as ammonium centers counter-balancing the 2-charge of the $\{V_6O_{19}\}$ unit.

Figure 1C:
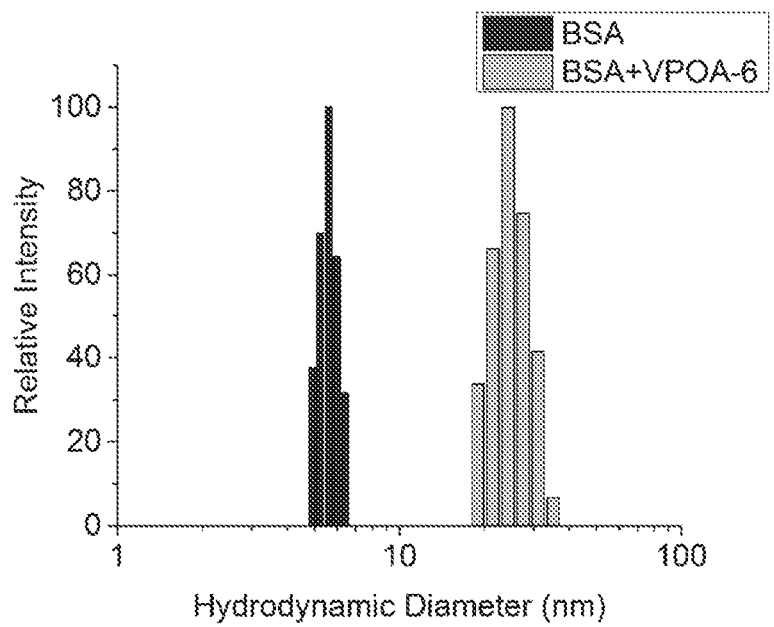
FIG. 1C shows data from dynamic light scattering (DLS) measurements of 2% wt. solution of bovine serum albumin (BSA) and the addition of VPOA-6 (final concentration of 20 µM). The hydrodynamic diameter of BSA is 5.6±0.34 nm and the size increased to 25±4.18 nm after VPOA-6 addition.

Crystallographically, VPOA-6 has D3h symmetry and is sufficiently small to be quite hard to image using transmission electron microscopy (TEM). Small-angle X-ray scattering (SAXS) experiment successfully revealed that the solid structure of VPOA-6 remains in aqueous solution. Interestingly, SAXS also demonstrated that a large nanoassembly exists when bovine serum albumin (BSA) is present in solution, indicating the association of BSA with VPOA-6. Dynamic light scattering (DLS) showed the consistent result: a stable monodispersed suspension of BSA and VPOA-6 adducts formed with a hydrodynamic size of ca. 25 nm in aqueous solutions (FIG. 1C). The noncovalent binding of the nanocluster to albumin might play a role in in vivo transport.

Stability of VPOA-6

The stability of drugs, especially nanomedicines, is a factor ensuring the identity, potency, and purity of the drug during applications. Multiple physicochemical methods including UV-vis, FT-IR and different nuclei NMR establish that VPOA-6 is stable under the conditions or in different media used in this study including cell culture media, DMSO and PBS (1× or 10× and pH 7.4) buffer solutions.

Evaluation of VPOA-6 Activity for Catalyzing Glutathione Oxidation

Vanadium-containing compounds have extensive redox properties and consequently catalyze several organic substrate oxidations via free radical mechanisms. VPOA-6 is a highly efficient catalyst for oxidizing glutathione (GSH), the primary intracellular antioxidant, through both aerobic oxidation and peroxidation under physiologically relevant conditions. Glutathione is the most abundant cellular reducing metabolite with concentrations in the millimolar range and is regarded as the primary mechanism for protecting cells against oxidative stress during proliferation and growth. In order to evaluate the inherent catalytic capability of VPOA-6, proton nuclear magnetic resonance (1H NMR) spectroscopy was used to monitor the in vitro oxidation of GSH. Two reactions were designed for this purpose, GSH reacting with air ($O_2$) and, separately, GSH reacting with peroxide ($H_2O_2$) in PBS buffer (1× pH 7.4) at 37° C.

Figure 2A:
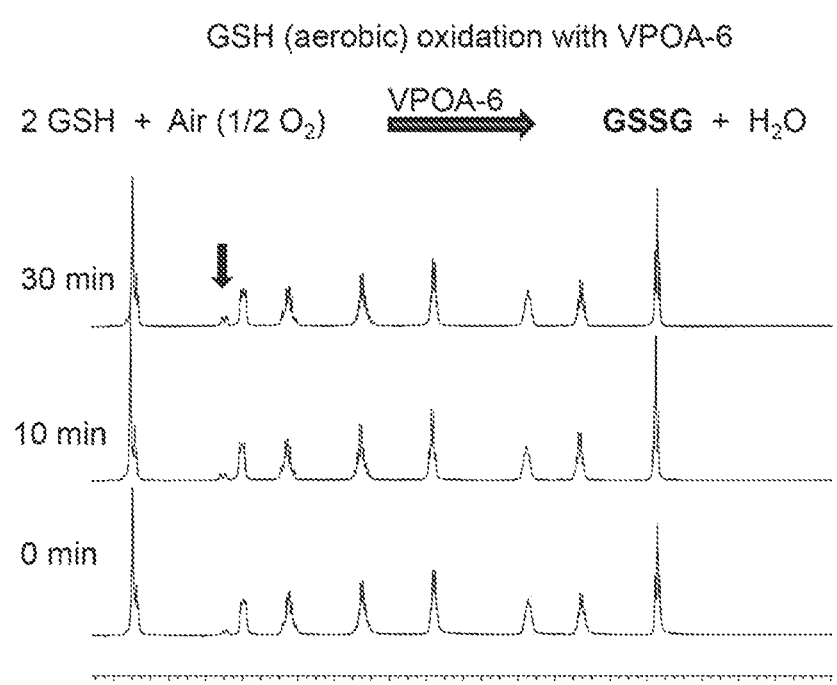
FIG. 2A shows data on GSH oxidation in the air with VPOA-6 under cell culture conditions. $^1$H NMR was used to monitor this reaction. GSH (10 mM) in deuterated PBS (1×, pH 7.4) solution at 37° C. in a cell culture incubator. The arrow on the top spectrum indicates the chemical shift of a dominant peak (absent here) in the oxidation product (GSSG).
Figure 2B:
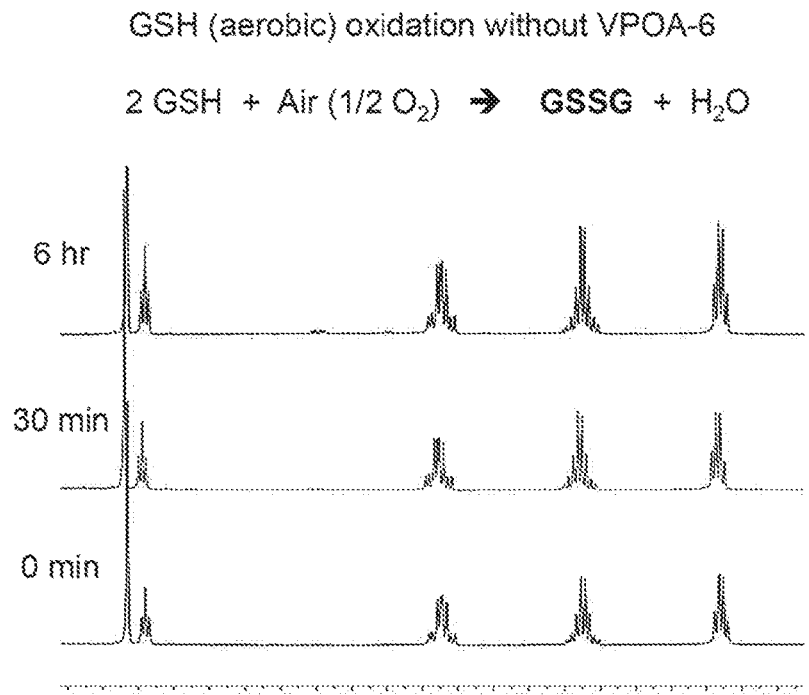
FIG. 2B shows data without VPOA-6.

Experimental results indicate that the reduced GSH is quickly converted by VPOA-6 to its oxidized form, GSSG, in the presence of air in 30 minutes (FIG. 2A). In contrast, GSH remains unchanged under otherwise identical conditions but in the absence of VPOA-6 (FIG. 2B). In the presence of $H_2O_2$ and VPOA-6, GSH quickly transforms to oxidative intermediates, as indicated by the disappearance of GSH peaks and the appearance of multiple new peaks in the dynamic NMR spectra after the first 10 minutes. The NMR spectrum remains unchanged after 30 minutes and exhibits the distinct peaks for the over-oxidized product, GS(=O)SG, indicating that VPOA-6 may catalytically divert GSH into this product more efficiently than into the natural metabolite GSSG in cells. Over-oxidation suppresses the regeneration of GSH and associated metabolic disorders. In contrast, GSH was specifically oxidized to GSSG without VPOA-6 under the same conditions. In addition, VPOA-6 efficiently catalyzes ascorbic acid oxidation in presence of either air or peroxide under the physiological conditions. The efficient oxidative conversion of the cellular antioxidants by VPOA-6 substantiates that this nanodrug is a capable catalytic species and implicates its likely involvement in GSH metabolism and ROS generation in vivo.

VPOA-6 Selectively Kills Cancer Cells but not Normal Cells

The effective catalytic oxidation of cellular antioxidants by VPOA-6, led to an assessment of the viability of both cancer and normal cell lines in the presence of VPOA-6. Four VPOA analogues (FIG. 1B) for selectivity of VPOA-6 in killing cancer cells by cytotoxicity towards the fast-growing KB-3-1 cancer cell line. All four hexavanadate analogues exhibit micromolar cytotoxicity, with VPOA-6 being the most effective: $IC_{50}$=3.45 μM.

| | KB-3-1 Cancer cell line | | | | |
|---|---|---|---|---|---|
| | VPOA-6 | VPOA-NO$_2$ | VPOA-CH$_3$ | VPOA-OH | TBA Cl |
| $IC_{50}$ (μM) | 3.45 ± 0.92 | 13.71 ± 0.15 | 16.21 ± 0.08 | 21.03 ± 1.47 | 289.34 ± 12 |

Figure 3:
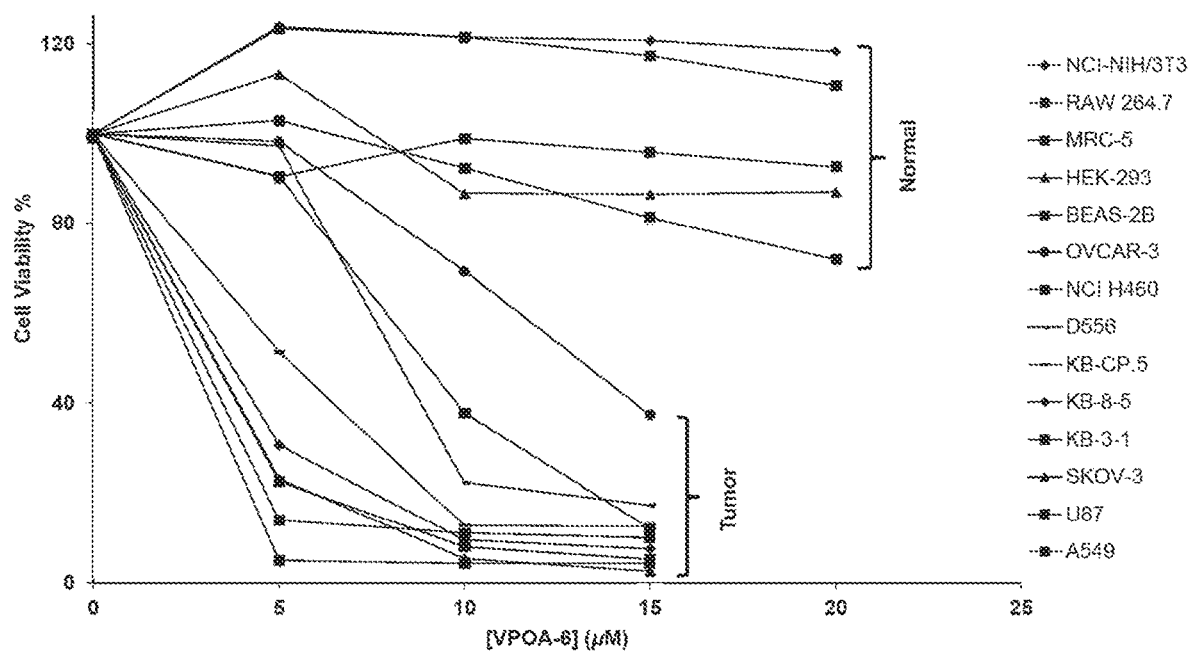
FIG. 3 shows data indicating selective killing effect of VPOA-6 on cells. VPOA-6 treatment induces cell death in cancer cells (Tumor) but not in normal proliferating cells (Normal). A variety of cancer or normal cells were grown in 96-well plates and treated with VPOA-6 at 0-20 µM for 72 h. Cytotoxicity was measured using cell counting kit-8. OVCAR-3 (human ovarian carcinoma), NCI-H460 (human non-small cell lung carcinoma), D556 (Medulloblastoma), KB-CP.5 (cisplatin resistant adenocarcinoma cells), KB-8-5 (cervical cancer cell), KB-3-1 (head/neck carcinoma), SK-OV-3 (ovary: ascites, adenocarcinoma); U-87 (human brain glioblastoma), A459 (human lung carcinoma).

The effect of VPOA-6 on the viability of a spectrum of cancer cells and normal proliferating cells were then evaluated. Significantly, VPOA-6 selectively kills a wide range of human cancer cell lines while showing no cytotoxicity in normal proliferating cells (FIG. 3). In particular, four major types of human cancer cell lines, A549 (lung), U87 (brain), SKOV-3 (ovarian), and KB-3-1 (cervical), are highly sensitive to VPOA-6 with $IC_{50}$ values below 5 μM. These $IC_{50}$ values are close to those of cisplatin: 4.4 (SKOV-3) and 2.8 (KB-3-1) μM, respectively.

One aspect of selectivity is the efficacy ratio of a therapeutic agent for normal cells versus cancer cells. In sharp contrast to cancer cells, human embryonic kidney HEK 293, human lung MRC-5, and human bronchus BEAS-2B normal cells are viable at VPOA-6 concentrations up to 20 μM. Additionally, TUNEL and Annexin V-PE staining assays both show dramatic apoptosis of the cancer cells when treated with the drug; whereas, these normal proliferating cells remain alive. These results collectively suggest that the therapeutic effect of VPOA-6 may fall in a well-defined cytotoxic window where cancer cells are killed very effectively while normal cells remain healthy. A fluorescent-labeling technique successfully images the uptake of VPOA-6 into living cells showing that cancer cells readily internalize this nanodrug within 8 hr even at very low concentrations (1 μM).

VPOA-6 Kills Drug-Resistant Cancer Cells

Figure 4A:
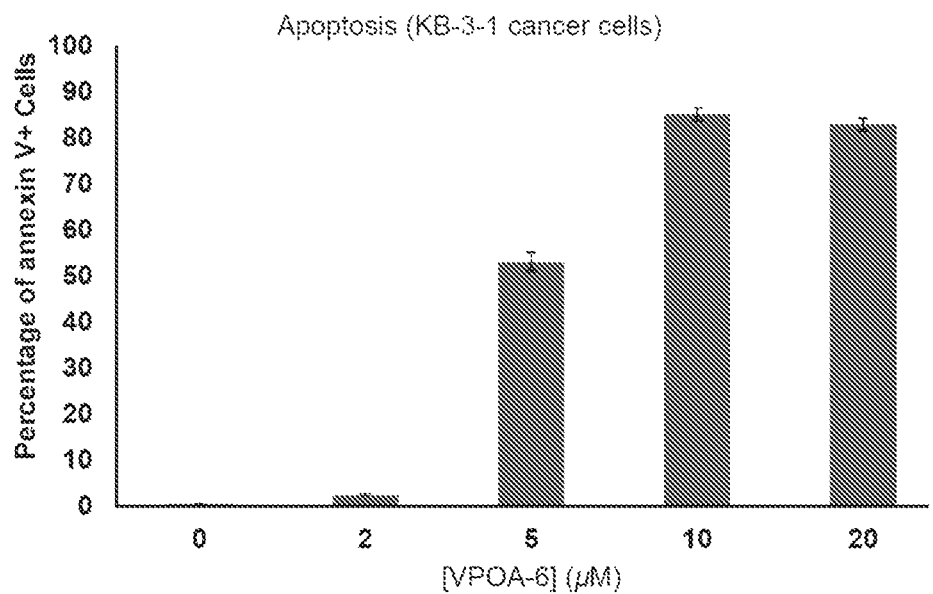
FIG. 4A shows data on apoptosis of KB-3-1 cancer cells induced by VPOA-6. Dose-dependent apoptosis induced by VPOA-6 in KB-3-1 cancer cells. Apoptosis was measured after cancer cells were treated with the drug for 48 hr.
Figure 4B:
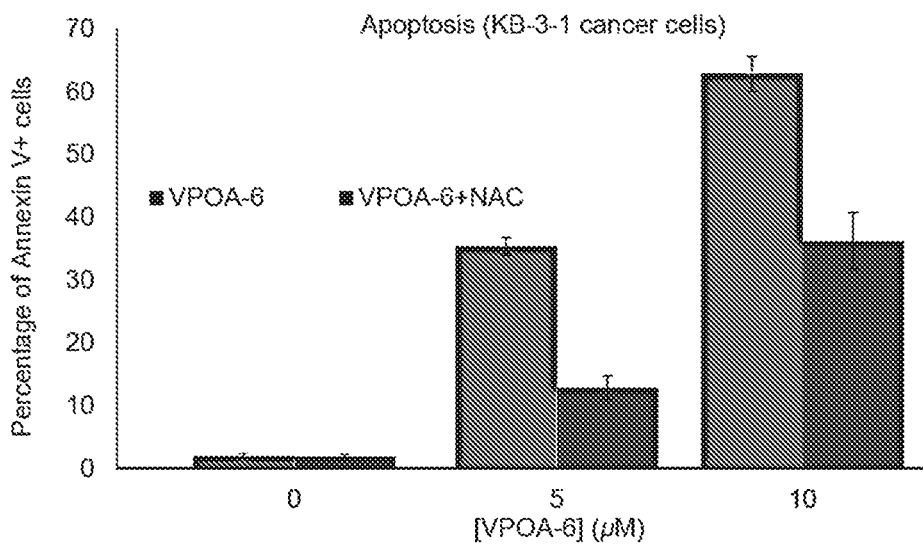
FIG. 4B shows data indication a ROS scavenging agent NAC rescues the VPOA-6-induced apoptosis in KB-3-1 cancer cells. Cancer cells were cultured with VPOA-6 (5 or 10 µM) with or without NAC (3 mM) for 48 hr before apoptosis measurement.
Figure 4C:
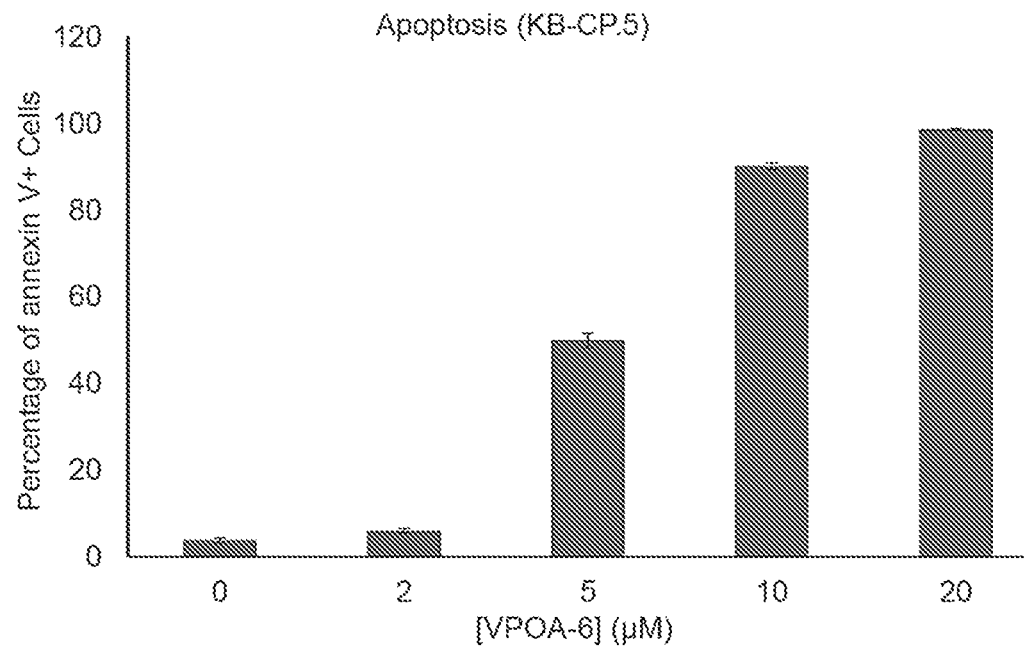
FIG. 4C shows data on the apoptosis of cisplatin-resistant KB-CP.5 cancer cells induced by VPOA-6. Apoptosis was measured after cells treated with VPOA-6 at different concentrations for 48 hr.
Figure 4D:
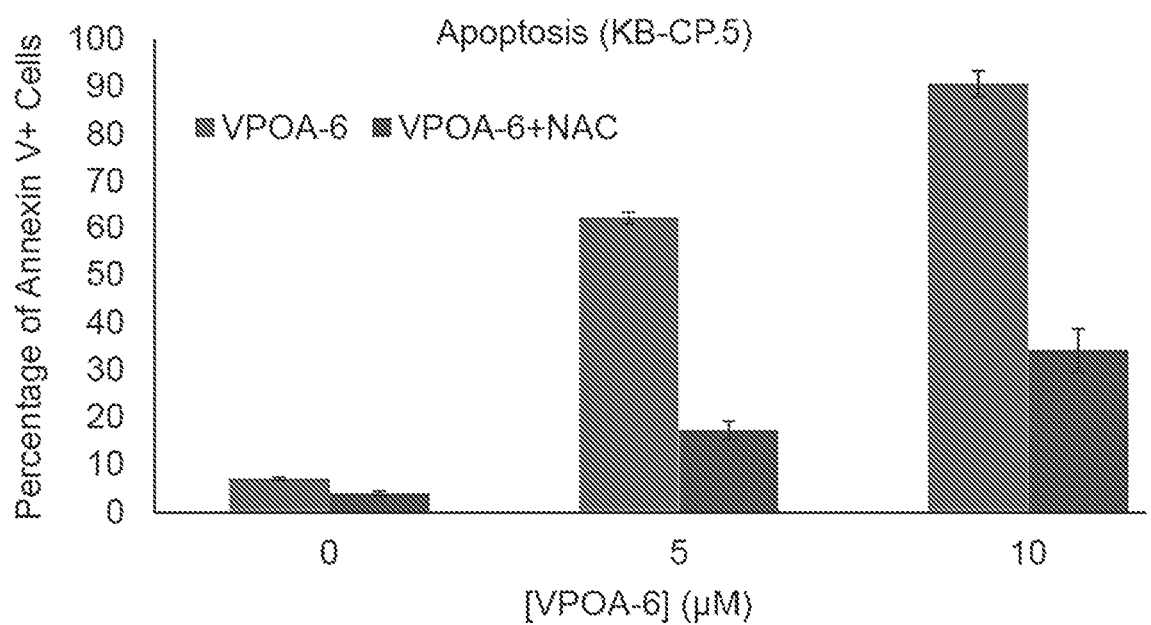
FIG. 4D shows data on the apoptosis of cisplatin-resistant KB-CP.5 cancer cells induced by VPOA-6. NAC rescues the VPOA-6-induced apoptosis in KB-CP.5 cancer cells. Cancer cells were cultured with VPOA-6 (5 or 10 µM) with or without ROS scavenging agent NAC (3 mM) for 48 hr before apoptosis measurement.

More surprisingly, this nanocluster retains its high cytotoxicity to drug-resistant cancers. The high incidence of drug resistance is a major challenge in treatment of relapsed and refractory cancers. In the test of the highly aggressive human cervical carcinoma KB-3-1 cancer cells and its drug-resistant derivatives KB-8-5 and KB-CP.5, all the three cell lines showed similar sensitivity to VPOA-6 at micromolar concentrations regardless of the level of their drug-resistance (FIG. 3). When compared to its parental KB-3-1 cancer cell line (FIGS. 4A and 4B), for example, KB-CP.5 cancer cells are ca. 40-fold more resistant to cisplatin and also cross-resistant to many other anticancer drugs that are in heavy clinical use such as carboplatin, methotrexate, vinblastine, adriamycin, puromycin and actinomycin D. In dramatic contrast to cisplatin, VPOA-6 effectively kills KB-CP.5 ($IC_{50}$=5.53 μM) (FIGS. 4C and 4D) and KB-8-5 ($IC_{50}$=3.70 μM), which shows this nanocluster retains potency to cisplatin-resistant cancers with the same micromolar level toxicity toward cisplatin-sensitive cancers. The resistance of tumor cells to platinum-based chemotherapeutics is known to be associated with increased GSH levels; whereas cancer cells with high GSH levels are frequently more sensitive to drugs that affect GSH43. The similar degree of inhibition of cell proliferation for both drug-resistant and their parental cancer cells indicates that VPOA-6 may perturb the regulation of cellular GSH homeostasis, a distinct mechanism from that of Pt-based drugs. The possible combination therapy of VPOA-6 and cisplatin may offer a promising treatment modality that overcomes the intrinsic and acquired resistance of cancer cells to cisplatin44.

The toxicity profile of VPOA-6 is distinct from that simple vanadium salts and other polyoxoanions. Interestingly and significantly, unlike the zwitterionic VPOA-6 nanocluster, the readily available vanadium compounds, Na3VO4, NaVO3, and V2O5 are active but nonselective. Each of these simple compounds kills both KB-3-1 and normal cells. This finding indicates that the zwitterionic form of VPOA-6 may possess some unique features that explain the cell killing selectivity. Finally, the activity of VPOA-6 with that of the other nanoscale metal oxide species ($Na_3PMo_{12}O_{40}$, $K_5AlW_{12}O_{40}$, $Na_6P_2Mo_{18}O_{62}$ and $Na_6P_2W_{18}O_{62}$) were compared. None of these latter species showed any activity against KB-3-1 cells at concentrations below 50 μM.

Mechanistic Studies on the Activity and Selectivity of VPOA-6 for Killing of Cancer Cells The marked selectivity of VPOA-6 for killing cancer cells versus normal proliferating cells led further evaluations of the mechanism of specific cytotoxicity. Cancer cells are more sensitive to changes in redox status. Given the potent catalytic oxidative removal of GSH by VPOA-6, this drug may specifically induce cancer cell death based on the distinct redox statuses of cancer versus normal cells. Indeed, VPOA-6 inhibits cell proliferation by interference with redox homeostasis in cells, which leads to the breakdown of the cellular defense by induced oxidative stress.

ROS Tests

Transition-metal-based polyoxoanions sometimes have the ability to catalyze a range of oxidation reactions and to generate the free radicals under mild conditions. Although it is not intended that embodiments of this disclosure be limited by any particular mechanism, it is quite reasonable that VPOA-6 may enhance the production or accumulation of reactive oxygen species (ROS) in cancer cells leading to oxidative stress and cell death. To test this hypothesis, the levels of total cellular ROS ($H_2O_2$) were measured using flow cytometry. After exposure to VPOA-6 (5 and 10 KB-3-1 cells display a significant surge in ROS levels compared with non-treated KB-3-1 cells. To assess the functional importance of ROS induction in the VPOA-6-treated KB-3-1 cells, cells were co-treated with both VPOA-6 (5 and 10 μM) and a ROS scavenger N-acetyl-L-cysteine (NAC, 3 mM). NAC reduces ROS and the cell killing by VPOA-6.

These results are consistent with the apoptosis test, showing that NAC can also rescue the drug-treated cells from apoptosis. FACS confirms the viability of cells pretreated with NAC and also demonstrates a variable reduction in intracellular ROS levels. Further, a dramatic ROS increase was observed and the resulting remarkable apoptosis in the drug-resistant KB-CP.5 cancer cell when treated with VPOA-6 but not cisplatin. Due to the marked surge of ROS, DNA damage was also detected in the late apoptosis of cells treated with VPOA-6. Consistent with these results, hydrogen peroxide ($H_2O_2$), a cell permeable ROS, acted synergistically with VPOA-6 in killing cancer cells. In contrast, VPOA-6-treated normal cells experienced ROS increase but did not show obvious apoptosis. Taken together, these results indicate that the selective killing of cancer cells by VPOA-6 is mediated by the induction of ROS.

In Vivo Studies of VPOA-6

Figure 5:
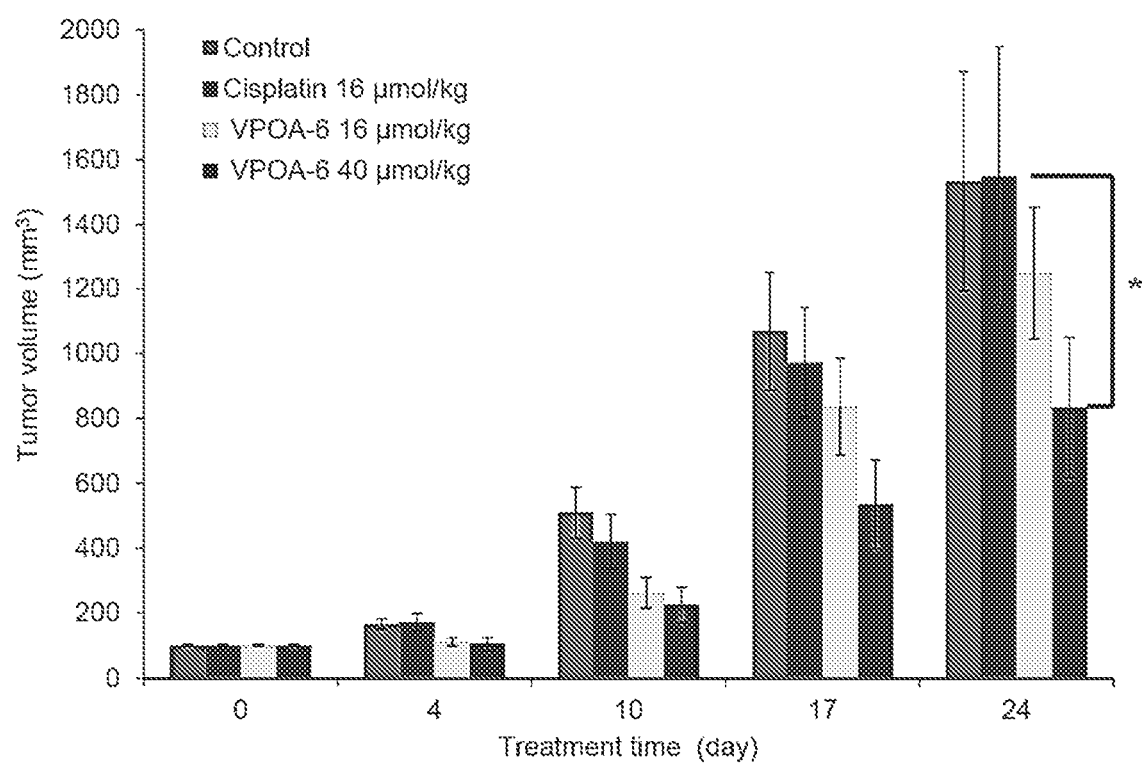
FIG. 5 shows data on the evaluation of VPOA-6 antitumor efficacy. In vivo antitumor effect of VPOA-6. Inhibition of human head-and-neck KB-3-1 tumor growth by VPOA-6 treatment in tumor-bearing mice. When tumors had grown to 5-6 mm in diameter, VPOA-6 (16 or 40 µmol/kg) or cisplatin (16 µmol/kg) was intraperitoneally (i.p.) administered (n=7-8 mice per group, *p=0.04, t-test) weekly for 24 days. Mice were then euthanized, vital organs collected and processed for histological examination.

Human cervical cancer is one of the most aggressive forms of human cancer. VPOA-6 was confirmed to be quite effective using both intraperitonial (i.p.) or intravenously (i.v.) administration protocols against KB-3-1 human cervical carcinoma in a xenograft mouse model (FIG. 5A). In sharp contrast, the cisplatin-treated group at the same dose under the identical administration schedule showed no inhibition. Specifically when using i.p. administration, the tumor volume of VPOA-6-treated group at a dose of 40 μmol/kg was less than 40% of that control group at the end point. Also, treatment with VPOA-6 at a much lower dose of 16 μmol/kg already clearly demonstrated the antitumor effect. In contrast, treatment of cisplatin at 16 μmol/kg, a dose that is close to its $LD_{50}$ value (22 μmol/kg) in mice, did not exhibit any tumor inhibition effect under the same conditions. I.v. administration of VPOA-6 also exhibited more significant tumor inhibition. All these in vivo results substantiate that VPOA-6 is an effective anticancer drug exhibiting marked antitumor activity. Evaluation of VPOA-6 side effects. A central issue in developing new chemotherapeutics is to minimize the side effects associated with the non-specific interaction of the drugs with normal organ tissues.

Compared with the control group, all mice in the VPOA-6-treated groups at the two dosage levels above using two administration techniques, remained healthy throughout the treatment period. No poor appearance and gross weight loss were observed under our administration schedule. In comparison, the mice in the cisplatin-treated group exhibited deteriorated health and severe body weight loss after each administration. Increased dosages of cisplatin resulted in widespread death. In addition, immunohistological examination of vital organs of drug-treated mice revealed substantial changes in the morphologies of the organ tissues in the cisplatin-treated group but no obvious changes in the VPOA-6 group. Nephrotoxicity, the notorious dose-limiting side effect of cisplatin leading to severe renal damage, was not observed with VPOA-6. Significantly, cell viability studies of HEK 293, a normal human kidney cell line, show that cisplatin is very toxic, whereas VPOA-6 is much less so. The collective studies show conclusively that VPOA-6 is a rare example of an inorganic therapeutic with potent antitumor activity with a far more favorable chemotherapeutic profile than cisplatin.

VPOA-6 Significantly Suppresses the Growth of a Broad Spectrum of Cancer Cells Including Drug-Resistant Types in the Micromolar Range while Exhibiting No Cytotoxicity to Normal Cells Cell lines used in this study are as follows. A549, non-small cell lung cancer; U87, glioblastoma cell; SKOV-3, ovarian carcinoma cell (resistant to tumor necrosis factor and to several cytotoxic drugs including diphtheria toxin, cis-platinum and Adriamycin); KB-3-1, cervical carcinoma cell; KB-8-5, multi-drug resistant cervical carcinoma cell; KB-CP.5, cisplatin-resistant cervical carcinoma cell; D556, medulloblastoma cell; NCI-H460, large cell lung carcinoma; OVCAR-3, ovarian carcinoma (drug resistant; resistant to clinically relevant concentrations of adriamycin, melphalan and cisplatin); BEAS-2B, bronchial epithelial cells; HEK-293, embryonic kidney cells; MRC-5, lung fibroblast cells; RAW264.7, macrophage cells; and NCI-NIH/3T3, fibroblast cells.

Cell viability ($IC_{50}$) of cancer cells and normal cells toward zwitterionic VPOA-6

| | Cervical cancer cell line | | |
|---|---|---|---|
| | KB-3-1 | KB-8-5 | KB-CP.5 |
| $IC_{50}$ (μM) | 3.45 ± 0.92 | 3.70 ± 0.15 | 5.53 ± 0.09 |
| | Brain cancer cell line | | |
| | U87 | D556 | |
| $IC_{50}$ (μM) | 0.80 ± 0.10 | 7.36 ± 0.54 | |
| | Lung cancer cell line | | |
| | A549 | NCI-H460 | |
| $IC_{50}$ (μM) | 1.13 ± 0.02 | 8.69 ± 0.91 | |
| | Ovarian cancer cell line | | |
| | SKOV-3 | OVCAR-3 | |
| $IC_{50}$ (μM) | 3.12 ± 0.05 | 10.79 ± 0.49 | |

The invention claimed is:

1. A method of treating cancer comprising administering an effective amount of $[V_6O_{13}\{(OCH_2)_3CNH_3\}_2]$, or salts thereof to a subject in need thereof.

2. The method of claim 1, wherein the subject is diagnosed with cancer.

3. The method of claim 1, wherein the cancer is leukemia, lymphoma, melanoma, glioblastoma, cervical, ovarian, colon, breast, gastric, lung, skin, ovarian, pancreatic, prostate, head, neck, bladder, and renal cancer.

4. The method of claim 1, wherein the polyoxometalate complex is administered in combination with a second chemotherapeutic agent.

5. The method of claim 4, wherein the second chemotherapy agent is a platinum-based antineoplastic, cisplatin, carboplatin, oxaliplatin, nedaplatin, triplatin tetranitrate, phenanthriplatin, picoplatin, satraplatin, or combinations thereof.

* * * * *